United States Patent

Haisch et al.

(10) Patent No.: US 8,810,907 B2
(45) Date of Patent: Aug. 19, 2014

(54) SURGICAL MICROSCOPE SYSTEM AND METHOD

(75) Inventors: Michael Haisch, Aalen (DE); Christoph Hauger, Aalen (DE); Hartmut Wolf, Oberkochen (DE); Joachim Hug, Oberkochen (DE); Schwarz Brigitta, Oberkochen (DE); Gerhard Gaida, Aalen (DE); Andreas Raabe, Frankfurt am Main (DE)

(73) Assignee: Carl Zeiss Meditec AG, Jena (DE)

( * ) Notice: Subject to any disclaimer, the term of this patent is extended or adjusted under 35 U.S.C. 154(b) by 135 days.

(21) Appl. No.: 13/193,759

(22) Filed: Jul. 29, 2011

(65) Prior Publication Data

US 2012/0194663 A1 Aug. 2, 2012

Related U.S. Application Data

(62) Division of application No. 12/380,286, filed on Feb. 25, 2009, now Pat. No. 8,189,201, which is a division of application No. 10/650,038, filed on Aug. 28, 2003, now Pat. No. 7,580,185.

(30) Foreign Application Priority Data

Aug. 28, 2002 (DE) .................................. 102 39 514
Feb. 3, 2003 (DE) .................................. 103 04 268

(51) Int. Cl.
*G02B 21/06* (2006.01)

(52) U.S. Cl.
USPC .......................................... 359/388; 359/385

(58) Field of Classification Search
None
See application file for complete search history.

(56) References Cited

U.S. PATENT DOCUMENTS

| | | | |
|---|---|---|---|
| 3,877,712 A | 4/1975 | Weckeiser | |
| 3,971,951 A | 7/1976 | Rikukawa et al. | |
| 4,427,889 A | 1/1984 | Müller | |
| 4,786,154 A | 11/1988 | Fantone et al. | |

(Continued)

FOREIGN PATENT DOCUMENTS

| | | | |
|---|---|---|---|
| DE | 36 04 815 A1 | 8/1987 | |
| DE | 43 20 579 C2 | 12/1993 | |

(Continued)

OTHER PUBLICATIONS

English translation of Japanese Office Action dated Mar. 13, 2012 in corresponding Japanese Application No. 2010-006800.

(Continued)

*Primary Examiner* — Arnel C Lavarias
(74) *Attorney, Agent, or Firm* — Potomac Patent Group PLLC

(57) ABSTRACT

A microscopy system and method allow observing a fluorescent substance accumulated in a tissue. The tissue can be observed at a same time both with visible light and with fluorescent light. It is possible to observe a series of previously recorded fluorescent light images in superposition with the visible light images. An end of the series of images may be automatically determined. A thermal protective filter may be inserted into a beam path of an illuminating system at such automatically determined end of the series. Further, the fluorescent light image may be analyzed for identifying a coherent fluorescent portion thereof. A representation of a periphery line of the coherent portion may be generated, and depths profile data may be obtained only from the coherent portion. An illuminating light beam for exciting the fluorescence may be modulated for improving a contrast of fluorescent images.

22 Claims, 5 Drawing Sheets

(56) References Cited

U.S. PATENT DOCUMENTS

| | | |
|---|---|---|
| 4,786,155 A | 11/1988 | Fantone et al. |
| 5,127,730 A | 7/1992 | Brelje et al. |
| 5,493,109 A | 2/1996 | Wei et al. |
| 5,795,295 A | 8/1998 | Hellmuth et al. |
| 5,827,190 A | 10/1998 | Palcic et al. |
| 5,845,639 A | 12/1998 | Hochman et al. |
| 5,865,829 A | 2/1999 | Kitajima |
| 6,169,816 B1 | 1/2001 | Ravkin |
| 6,212,425 B1 | 4/2001 | Irion et al. |
| 6,236,881 B1 | 5/2001 | Zahler et al. |
| 6,259,807 B1 | 7/2001 | Ravkin |
| 6,262,837 B1 | 7/2001 | Nagano et al. |
| 6,293,911 B1 | 9/2001 | Imaizumi et al. |
| 6,371,908 B1 | 4/2002 | Furusawa et al. |
| 6,429,936 B1 | 8/2002 | Scaduto |
| 6,470,124 B1 | 10/2002 | Le Gargasson et al. |
| 6,496,267 B1 | 12/2002 | Takaoka |
| 6,721,590 B2 | 4/2004 | Ohishi et al. |
| 6,747,280 B1 | 6/2004 | Weiss |
| 7,236,251 B2 | 6/2007 | Takaoka |
| 7,580,185 B2 | 8/2009 | Haisch et al. |
| 8,189,201 B2 * | 5/2012 | Haisch et al. ............... 356/497 |
| 8,300,309 B2 * | 10/2012 | Haisch et al. ............... 359/385 |
| 2003/0218755 A1 | 11/2003 | Wei et al. |
| 2005/0182321 A1 | 8/2005 | Frangioni |
| 2010/0097618 A1 | 4/2010 | Haisch et al. |
| 2010/0110538 A1 | 5/2010 | Steffen et al. |

FOREIGN PATENT DOCUMENTS

| | | | |
|---|---|---|---|
| DE | 199 19 943 A1 | 4/1999 | |
| JP | 410325798 A | 8/1998 | |
| JP | 10-325798 A | 12/1998 | |
| JP | 10325798 A | 12/1998 | |
| JP | 2001-25400 A | 1/2001 | |
| JP | 2001025400 A | 1/2001 | |
| JP | 2002-98899 A | 4/2002 | |
| JP | 2002098899 A | 4/2002 | |
| JP | 2002-514304 A | 5/2002 | |
| JP | 2002514304 A | 5/2002 | |
| WO | 00/16151 A1 | 3/2000 | |
| WO | 00/36451 A1 | 6/2000 | |
| WO | 00/67635 A1 | 11/2000 | |
| WO | 00/71162 A2 | 11/2000 | |
| WO | 01/22870 A1 | 4/2001 | |
| WO | 01/46459 A1 | 6/2001 | |
| WO | 2004/054439 A2 | 7/2004 | |

OTHER PUBLICATIONS

Gupta, M. et al., "Optical Coherence Tomography Correlated with Functional Fluorescence Imaging of the Atrio-Ventricular Node", European Conferences on Biomedical Optics, 2001, entire document.

Kuroiwa, T. et al., "Development and Clinical Application of Near-Infrared Surgical Microscope: Preliminary Report", Minim Invas Neurosurg 2001; 44: pp. 240-242.

Raabe, A. et al., "Near-Infrared Indocyanine Green Video Angiography: A New Method for Intraoperative Assessment of Vascular Flow", Neuro Surgery, vol. 52, No. 1, Jan. 2003, pp. 132-139.

Japanese Office Action in corresponding Japanese Application No. 2010-006800 mailed Feb. 26, 2013.

* cited by examiner

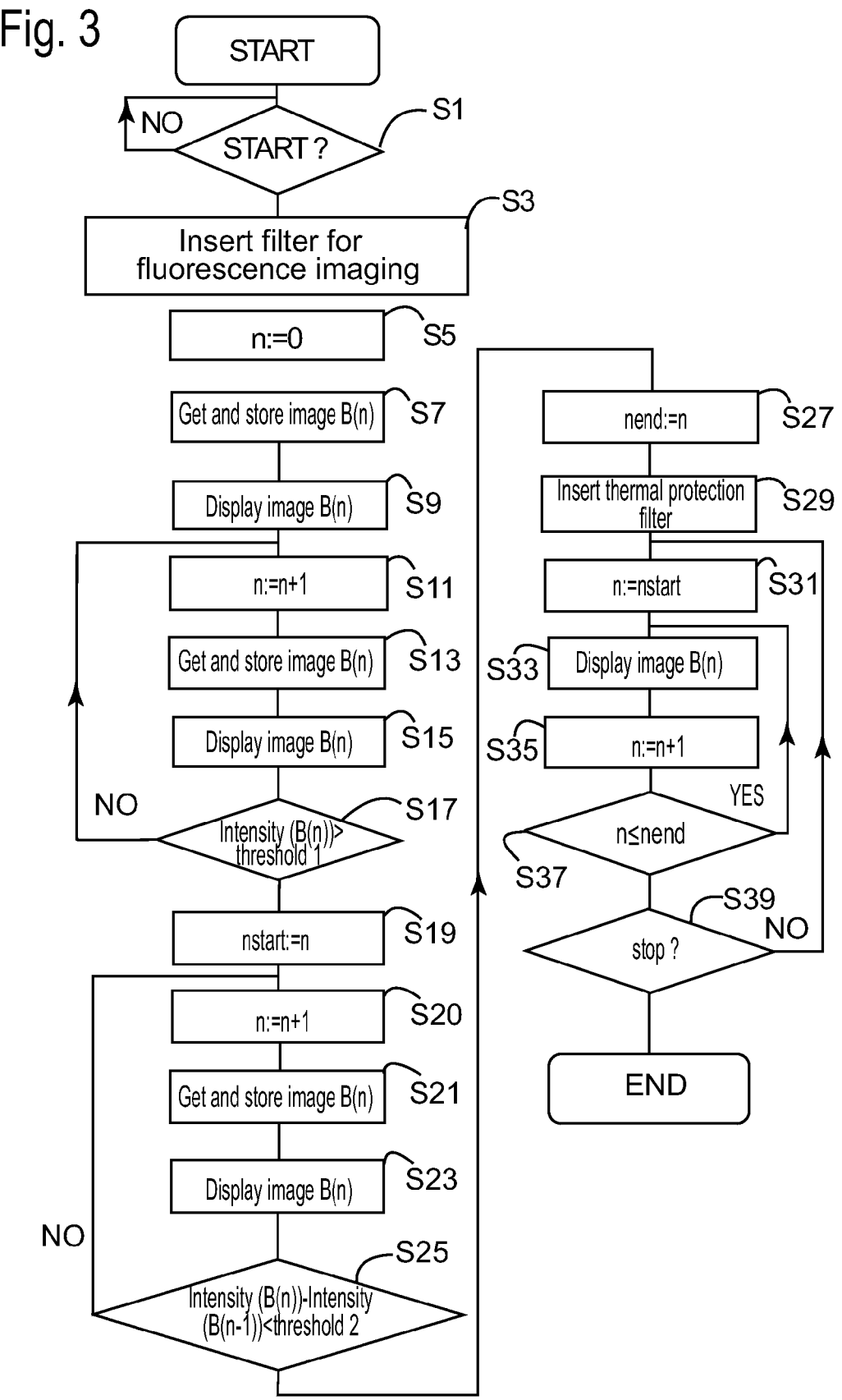

SURGICAL MICROSCOPE SYSTEM AND METHOD

TECHNICAL FIELD

The invention relates to a microscopy system and a microscopy method which may be in particular used for observing an emission of fluorescent light at wavelengths of the near infrared and/or infrared. Further the invention relates to a method of treating an aneurysm.

Fluorescent substances and fluorescent dyes showing a fluorescence at wavelengths in a region of the near infrared or infrared are used in medical applications for various purposes such as visualizing particular types of tissue, tissue structures and tissue functions. Herein, a fluorescent substance or dye or a precursor of such fluorescent substance or dye is applied to a patient under examination. The dye accumulates in particular types of tissue and tissue structures, and by observation of the fluorescent light such types of tissue and tissue structures, respectively may be visualized and identified by an observer. Optical tools are used to visualize the some times weak intensities of fluorescent light.

BRIEF DESCRIPTION OF RELATED ART

One example of a suitable fluorescent substance is indocyanine green (ICG). From the article by T. Kuroiwa et al., "Development and Clinical Application of Near-Infrared Surgical Microscope: Preliminary Report", Minim Invas Neurosurg 2001; 44: 240-242, there is known a method and system for observing the fluorescence of this substance. An excitation wavelength of the fluorescence of the substance is about 780 nm, and fluorescent emission wavelength is about 835 nm. For an observation of a tissue in which ICG has accumulated by a microscope, the tissue is illuminated with light of a main wavelength of 800 nm of a laser light source or of a halogen lamp. In a beam path of the illuminating light there is positioned a band-pass filter which allows only light having wavelengths between 760 nm and 810 nm which is light for exciting the fluorescence to pass there-through. The tissue is imaged onto a camera by a microscopy optics wherein a further band-pass filter which allows only light having wavelengths between 820 nm and 920 nm which is fluorescent emission light of ICG to pass there-through. An observation of images detected by the camera allows to identify those regions of the tissue in which the fluorescent substance has accumulated. It is, however, not possible to perceive surrounding regions of the tissue. Such surrounding regions would emit visible light under a suitable illumination. However, such illumination with visible light is not possible since the laser light source does not provide such light, and the band-pass filter in the beam path of the light source blocks such visible light from incidence on the tissue. A surgeon performing a surgical treatment of the tissue region has to illuminate the tissue region with visible light for perceiving an optical image of the tissue region with visible light in a first step, and he has to observed the fluorescent image thereafter for perceiving the fluorescent light in a subsequent second step. Further, an illuminating light beam of the laser light source and an illuminating beam for illuminating the tissue region with visible light are incident on the surface region under different angles such that both light beams generate different types of shadows on the tissue region. Such different shadows render it more difficult to correctly associate regions of the fluorescent image with regions of the visible image of the tissue region.

Such procedure is complicated and requires a high power of concentration of the observer since he must remember the image previously perceived at the respective different type of illumination.

The article of T. Kuroiwa et al., discloses an application of the ICG fluorescence for obtaining information about deep-seated tissues. The excitation and emission wavelengths ICG lie within the "optical window" of tissue, where absorption attributable to endogenous chmmophoreous is low. Near infrared light can therefore penetrate tissue to a depth of several millimeters to a few centimeters. According to the article, a near infrared fluorescence of vessels on the brain surface was observed through the dura mater. The article concludes that a stronger fluorescence emitted from the ICG will be necessary for the application to have practical use even imaging venous vessels.

A cerebral or intra-cranial aneurysm is a dilatation of an artery in the brain that results from a weakening of the inner muscular layer of a blood vessel wall. The vessel develops a "blister-like" dilation that can become thin and rupture out warning.

The vascular dilation itself is referred to as an aneurysm sac, and an entrance are that leads from the parent artery to the aneurysm sac is referred to as an aneurysm neck. According to a conventional surgical technique of medical therapy of the aneurysm, a clip is used to close the aneurysm sac. Thereafter, the surgeon has to verify that the aneurysm sac is completely closed and that a sufficient vascular flow is guaranteed in the parent artery and surrounding vessels.

According to a conventional technique the vascular flow is assessed by x-ray angiographic. For performing x-ray angiography, the surgical microscope which must be used for performing the surgery and positioning the clip has to be dismounted first, the x-ray apparatus has to be mounted thereafter, and the surgeon has to leave the room while the x-ray images are recorded. Development and interpretation of the x-ray image will take some ten minutes. Intra-operative x-ray angiography is often not used in practice for blood flow assessment due to the long duration until interpretation of the results. Further, an imaging resolution achievable with x-ray angiography is not sufficient for assessing blood flow in small vessels. Further, a complication rate associated with x-ray angiography is considered to be relatively high due to the necessity of applying a corresponding contrast agent via a catheter into an artery of the patient.

SUMMARY OF THE INVENTION

It is an object of the present invention to provide a method of surgical treatment of an aneurysm and allowing intraoperative observation and documentation of blood flow in small arterial vessels.

It is a further object of the present invention to provide microscopy system and a corresponding microscopy method which improve a performance of microscopic imaging in combination with a fluorescence at infrared or near infrared wavelengths.

According to a first aspect of the invention there is provided a method of treating an aneurysm of a patient, the method comprising clipping the aneurysm, injecting indocyanine green into the patient generating at least one fluorescence image of at least one artery adjacent to the clipped aneurysm, and assessing vascular blood flow of the at least one artery based on the at least one fluorescence image.

The method using ICG as a fluorescent substance for assessing the blood flow is simple and offers real time information on the patency of arterial and venous vessels of all relevant diameters including small arteries such as arteries of a diameter less than 0.5 mm, that are visible to the surgeons eye. An interpretation of the recorded images may be finished within one minute or less. Since ICG is not metabolized in the body and is excreted by the liver with a plasma half time of three to four minutes, the method may be repeated after five to ten minutes.

A detailed illustration of the method is given in the article of A. Raabe et al., Neurosurgery, 132, volume 52, number 1, January 2003 (www.neurosurgery-online.com). The full disclosure of this article is incorporated herein by reference.

According to a second aspect of the invention there is provided a microscopy system and method having an improved performance in microscopic imaging fluorescent light images at infrared or near infrared wavelengths.

According to a further embodiment the invention provides a microscopy system for visualizing a fluorescence of indocyanine green (ICG) wherein the microscopy system comprises a microscopy optics, a display system and an illumination system. The microscopy optics comprises a first beam path for imaging an object region onto a light detecting component of the first camera using light of a first range of wavelengths comprising an emission wavelength or fluorescent wavelength of indocyanine green. Thus, the first beam path is provided for generating fluorescent light images of the object region. The microscopy optics further comprises a second beam path for providing a magnified representation of the object region with light of wavelengths of a second range of wavelengths including at least visible light. Thus, the second beam path is provided for generating images of the object region in a visible region of the spectrum.

The display system displays the fluorescent light images superimposed with the visible light representations such that a user may perceive both the fluorescent light images and the visible light representations at a same time.

The illumination system provides at least one illuminating light beam directed to the object region. The at least one illuminating light beam includes light of the visible portion of the spectrum, in particular blue light and/or yellow light, and the illuminating light beam also includes light with an excitation wavelength of indocyanine green.

The inventors recognized that it is possible to observe the object region with both visible light and fluorescent light at a same time when using the system illustrated above. It is not necessary to perform a conventional switching between observations under visible light and observations under fluorescent light. Further, the provision of the visible light and the excitation light in a common illuminating light beam prevents different shadows generated with excitation light and visible light on a structured object, and substantially the same illumination conditions are provided for both the excitation light and the visible light.

According to a preferred embodiment the at least one illuminating light beam is generated by one single light source generating both the visible light and the light of an excitation wavelength of indocyanine green. The light source may comprise light sources such as a xenon lamp or a halogen lamp.

Herein, the inventors recognized that suitable light sources which are conventionally used for generating illuminating light beams of visible light are able to generate excitation light of indocyanine green with a sufficient intensity for recording fluorescent light images of the object region with a suitable camera. Provision of a separate light source, such as a laser light source, for excitation of the fluorescence of the indocyanine green, as it was used in the prior art, is no longer necessary.

According to a preferred embodiment, a filter is disposed in a beam path of the illuminating system which filter substantially blocks light at emission wavelengths of the fluorescent emission wavelengths of indocyanine green. It is thus possible to record fluorescent images of a high contrast.

According to a preferred embodiment the microscopy system is used in the method of treating the aneurysm. According to a further embodiment, the illumination system comprises a thermal protective filter eliminating light from the illuminating light beam having wavelengths such that they are not perceived by the human eye or that they are perceived with only a low efficiency and which mainly contribute to heating of the object under examination. Thus, an unnecessary heating of the object is effectively prevented. The thermal protective filter may be removed from the beam path of the illumination system when fluorescent light images of the object are to be recorded.

The filters of the illumination system may be transmissive filters or reflective filters.

According to a preferred embodiment the microscopy system is used in the method of treating the aneurysm.

According to a further embodiment the invention provides a microscopy system for visualizing a fluorescence of a fluorescent substance wherein the microscopy system comprises a microscopy optics, an image memory and a display system. The microscopy optics again comprises a first beam path for imaging a fluorescent light image of the object region onto a camera, and a second beam path for providing a representation of the object region with light including at least visible light.

The image memory is configured for storing image data representing fluorescent light images of the object region recorded during a time interval.

The display system is configured to display the visible light image of the object region superimposed with a series of images generated from the previously recorded and stored image data.

It is thus possible to display rapidly changing configurations of the object region which are visible in the fluorescent image merely during a short time. Such rapidly changing configurations in the image are displayed in the overlaying relation with the visible light image of the object region at a time after the rapid change in the configuration has already happened. The rapidly changing configurations may be repeatedly displayed or they may be displayed in slow motion.

According to a preferred embodiment the microscopy system is used in the method of treating the aneurysm.

For this purpose indocyanine green is applied to the patient by intravenous injection, and the process of the fluorescent substance entering the parent and surrounding vessels is observed with the camera. The process of entering the vessels may take 0.5 to 2 s. Herein it is important that the blood with the fluorescent substance enters the relevant vessels at a substantially same time.

If the fluorescence will become visible in a particular vessel later than in surrounding vessels this will be indicative that the particular vessel is partially blocked.

The above illustrated assessment of vascular flow may be easily performed by repeatedly displaying the image data recorded during the respective time interval and/or by displaying the image data in slow motion and in superposition with the visible light image of the object region.

If the fluorescent substance accumulates in the aneurysm sac this will be indicative of a non-complete blocking of the necessary aneurysm sac with the clip.

Preferably, the microscopy system comprises a controller for analyzing the stored images with respect to a beginning process of the fluorescent substance entering the relevant vessels. Such start of the process may be derived from a time at which intensities of the fluorescent light exceed a threshold at some locations in the images.

The controller may also determine an end of such process by analyzing changes in fluorescent light intensities from image to image, and if a saturation of increasing intensities is detected, an end of the process of fluorescent substances entering the relevant vessel will be decided. The controller may then supply only a subset of the stored image data to the display system. The subset will include those data after the start and/or before the end of the process of fluorescent substances entering the relevant vessels.

According to a preferred embodiment the microscopy system is used in the method of treating the aneurysm.

According to a further embodiment the invention provides a microscopy system for visualizing a fluorescent substance wherein the microscopy system comprises a microscopy optics, an illumination system and a display system. The microscopy optics again comprises a first beam path for imaging a fluorescent light image of the object region onto a camera, and a second beam path for a magnified imaging of the object region with visible light. The display system again displays the visible light image of the object region superimposed with the fluorescent light image of the object region generated from image data recorded with the camera.

The illumination system provides an illuminating light beam directed to the object region wherein the illuminating light beam includes light at an excitation wavelength of the fluorescent substance. The illuminating system comprises a light modulator for modulating an intensity of the light at the excitation wavelengths of the fluorescent substance. This results in a modulation of the fluorescence of the substance in time, and the fluorescent images detected by the camera also vary in time. Such known variation in time of the intensities is taken into account when generating the fluorescent light images with a high contrast. For instance, locations in the images detected by the camera may be determined which show varying intensities. Only those locations may be then represented with a higher intensity in the generated fluorescence image.

According to a preferred embodiment the microscopy system is used in the method of treating the aneurysm.

According to a further embodiment the invention provides a microscopy system comprising a microscopy optics, an illumination system and a controller. The microscopy optics again comprises a first and a second beam path which traverse a common objective lens of the microscopy optics. The first beam path images the object region onto a camera for generating image data representing the object region. The illumination system provides an illuminating light beam directed to the object region. A filter is disposed in a first position within the beam path of the illuminating light beam. The illuminating system further comprises an actuator for changing the position of the filter from a second position in which the filter is not disposed within the beam path to the first position.

The controller is configured to analyze the image data recorded with the camera, and to control the actuator for displacing the filter from the first position to the second position based on such analysis. The analysis may comprise a determination of light intensities at particular portions of the images recorded with the camera.

Preferably the filter is a filter of such type that it eliminates light having wavelengths greater than a predetermined wavelength from the illuminating light beam. The predetermined wavelength is preferably greater than 690 nm. Further, the predetermined wavelength is preferably smaller than 800 nm.

With such system it is possible to provide two different illumination modes wherein the system is automatically switched from one mode to the other mode based on an analysis of the images of the object region detected by the camera.

A preferred application of such microscopy system is in combination with the above-illustrated process of a fluorescent substance entering some particular vessels of interest. An end of such process is automatically detected. It is then possible to operate the system in a first illumination mode during the recording of the fluorescent light images wherein the illuminating light beam includes infrared light for excitation of the fluorescence. When the end of the process is detected the thermal protective filter is automatically disposed in the beam path of the illuminating system such that the system is operated in a second illumination mode in which thermal radiation including infrared light is removed from the illuminating light beam for preventing unnecessary thermal heating of the inspected object region.

According to a preferred embodiment the microscopy system is used in the method of treating the aneurysm.

According to a further embodiment the invention provides a microscopy system comprising a microscopy optics having a first beam path for generating fluorescent light images of the object region and a second beam path for providing a representation of the object region as seen with visible light, and a display system for displaying the presentations generated from the fluorescent images in superposition with visible light representations of the object regions. The microscopy system further comprises a controller which is configured to analyze the fluorescent light images for detecting coherent portions of the image in which intensities of the fluorescent light exceed a threshold. The controller then generates image data representing the fluorescent light image such that only peripheral lines of the coherent portions are visible in the representation. The user may then identify those portions of the object region in which the fluorescent intensity exceeds the threshold by perceiving the peripheral line. At the same it is possible for the user to perceive an interior of the coherent portion as a representation of the visible light image According to a preferred embodiment the microscopy system is used in the method of treating the aneurysm.

According to a further embodiment the invention provides a microscopy system having an interferometer apparatus for generating depth profile data representing an intensity of radiation of an analyzing light beam received back from an object. The analyzing light beam is directed to the object, wherein a location to which the analyzing light beam is directed on the object may be selected by control of a beam scanner.

Generation of such depth profile data is conventionally time consuming and, in particular, it is conventionally necessary to generate depth profile data at substantially all scanning positions within an object field of the microscopy system.

According to the invention, a microscopy system having an interferometer apparatus is provided, wherein the microscopy system comprises a camera for recording an image of the object with fluorescent light, and wherein a controller is provided for analyzing the recorded image and for determining an analyzing portion within the image. The analyzing portion comprises at least one coherent portion of the image recorded with the camera in which an intensity in the image exceeds a threshold. The controller may control the interferometer apparatus such that the depth profile data are only generated at locations within the analyzing region.

It is thus possible that the controller selects from the fluorescent light image a tissue type of interest for the particular application, such as cancerous tissue, in dependence of the fluorescent image. Those portions in the image in which the tissue type of interest is present are used as the analyzing region, and depth profile data are generated only for locations within the analyzing region. In portions outside of the analyzing region depth profile data are not generated.

It is thus not necessary that the user has to determine those portions at which depth profile data should be generated, and it is possible to obtain the depth profile data for portions of interest in a relatively short time.

Preferably, the interferometer apparatus for generating the depth profile data comprises an optical coherence tomography (OCT) apparatus.

BRIEF DESCRIPTION OF THE DRAWINGS

The forgoing as well as other advantageous features of the invention will be more apparent from the following detailed description of preferred embodiments of the invention with reference to the accompanying drawings. Herein

FIG. 3 is a flowchart for illustrating a microscopy method according to an embodiment of the invention;

DETAILED DESCRIPTION OF EXEMPLARY EMBODIMENTS

Figure 1:
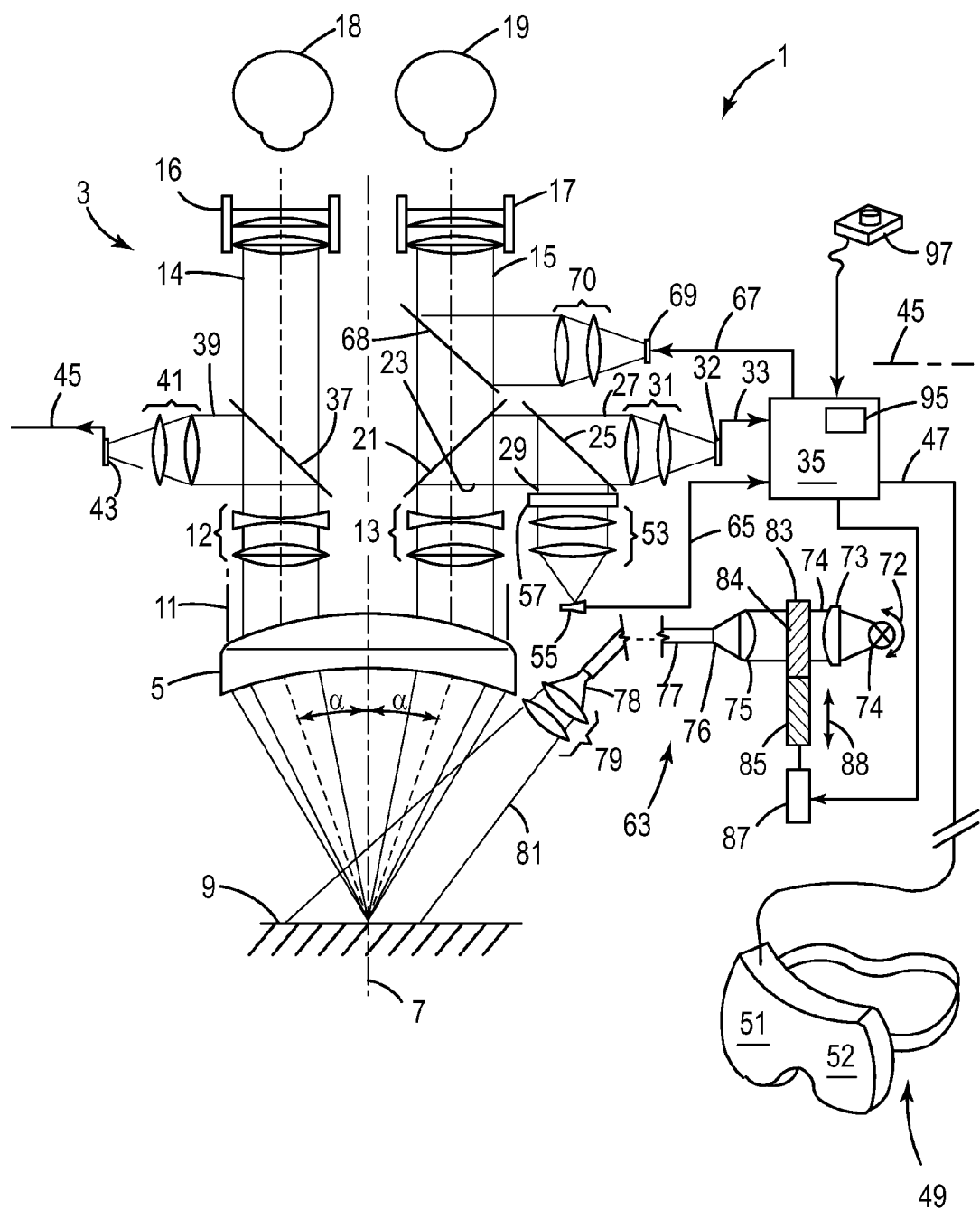
FIG. 1 shows a schematic representation of beam paths of a microscopy system according to an embodiment of the present invention.

FIG. 1 schematically shows a microscopy system 1 comprising a microscopy optics 3 including an objective lens 5 having an optical axis 7. An object 9 to be inspected is disposed in an object plane of objective lens 5. Light emanating from the object 9 is transformed by the objective lens 5 to form a parallel beam 11 in which two zoom systems 12, 13 are disposed at a distance from the optical axis 7. The zoom systems 12, 13 use partial beams 14 and 15 of the parallel beam 11 and supply the partial beams 14, 15 to oculars 16 and 17 through deflecting prisms (not shown in FIG. 1) of a body of a tube of the microscopy system 1. A user may perceive a magnified representation of the object 9 as an image looking into the oculars 16, 17 with his left eye 18 and right eye 19, respectively. The image perceived with the left eye 18 corresponds to an image when looking onto the object under an angle a with respect to the optical axis, and the image perceived with the right eye 19 corresponds to an image when looking onto the object 9 under an angle −a with respect to the optical axis 7, such that the user perceives a stereoscopic image of the object 9 with his both eyes 18, 19.

A partially transmissive mirror 21 is disposed in the partial beam 15 for branching off a portion of the light thereof as a beam 23. Beam 23 is split with a further beam splitter 25 to form beams 27 and 29. Beam 27 is supplied to a light sensitive element of a camera 32 through a camera adapter optics 31 such that the camera 32 detects an image of the object 9 under an observation angle −a with respect to optical axis 7. The images detected with camera 32 are transmitted as image data through a data line 33 to a controller 35.

A beam 39 is branched off from partial beam 14 by a partially transmissive mirror 37. Beam 39 is supplied to a light sensitive element of a further camera 43 through a camera adapter optics 41 such that camera 43 detects images of the object 9 under an observation angle a with respect to the optical axis 7. The images detected by camera 43 are supplied as image data to controller 35 through a data line 45. The controller transmits the images detected by cameras 32, 43 as image data through a line 47 to a head mounted display 49 which is carried by a user of the microscopy system 1 at his head such that integrated displays of the head mounted display 49 which are schematically indicated with reference numerals 51 and 52 in FIG. 1 provide respective images which may be perceived by the user with his left and right eyes, respectively.

Thus, a user who is not in a position of directly looking into the oculars 16, 17 may also perceive a stereoscopic representation of the object 9 by using the head mounted display 49 by observing representations of visible light images of object 9.

Figure 2A:
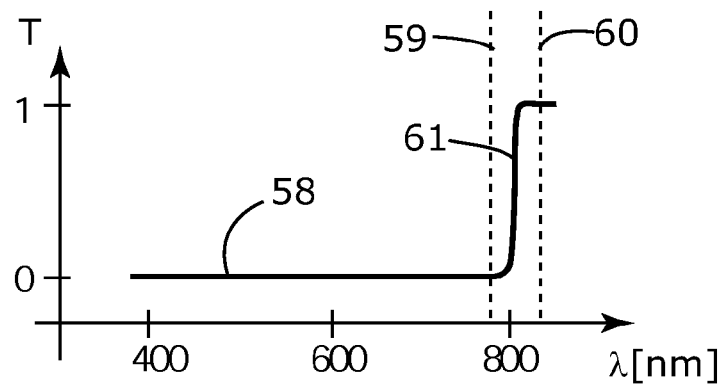
FIG. 2 shows transmission characteristics of filters which may be used in the microscopy system according to FIG. 1.

Beam 29 is supplied to a light sensitive element of a camera 55 through a camera adapter optics 53 such that camera 55 may detect an infrared image of the object. A filter 57 is disposed in beam 29. A transmission characteristic of filter 57 is schematically illustrated as a line 58 in FIG. 2a. A vertical line 59 in FIG. 2a further represents a maximum of an excitation spectrum of the fluorescent substance indocyanine green (ICG) at 780 nm. A vertical line 60 in FIG. 2a represents a corresponding maximum of a fluorescent emission spectrum of ICG at 835 nm. The transmission characteristic 58 of filter 57 shows a threshold 61 at about 810 nm. The filter 57 is substantially non-transmissive at wavelengths below the threshold, and the filter 57 is substantially transparent at wavelengths above the threshold. The camera 55 thus detects images of the object 9 which represent a distribution of the fluorescent substance within the object 9, provided that the fluorescence of the substance is excited with an illumination system 63 of the microscopy system 1 as further illustrated below.

The images detected with camera 55 are transmitted through a data line 65 to the controller 35. The controller 35 transmits the images detected with camera 55 as image data through a data line 67 to a LCD display 69. LCD display 69 represents the image data as an image which is superimposed with partial beam 15 by a collimating optics 70 and a partially transmissive mirror 68. The image of the display 69 may be perceived by the eye 19 of the user in superposition with the direct optical image of the object 9. The LCD display 69 represents the infrared light intensity distribution detected by camera 55 in a visible color such as green color. Green color may be advantageously used for representing the infrared image since human tissue forming the object 9 usually comprises green color in a relatively low amount.

The controller performs a data processing of the image data transmitted to display 51 of head mounted display 49 such that the display 51 displays the infrared light images detected by camera 55 superimposed with the visible light images detected by camera 32. Thus, the user wearing the display 49 at his head may also perceive with his right eye a superimposed representation of visible light images and infrared light images of the object.

Even though it is not illustrated in FIG. 1 for ease of reference and clarity, a further beam may be branched off from partial beam 14 supplied to the left eye 18. Such further beam may be supplied to a further infrared camera for generating images which are superimposed with the partial beam 14 of visible light as illustrated above for partial beam 15, LCD display 69, collimating optics 70 and partially transmissive mirror 68. The user will then perceive a stereoscopic infrared light image of the object 9. Image data generated by such additional camera may also be supplied to display 52 of head mounted display 49 such that also head mounted display 49 provides a stereoscopic representation of a distribution of the fluorescent substance within the object 9.

The illumination system 63 comprises a halogen lamp 71 a light source, a reflector 72 and a collimator 73, for generating a collimated light beam 74 which is directed through one or plural lenses 75 onto an entrance end 76 of an optical fiber bundle 77 for coupling light emitted from light source 71 into the fiber bundle 77. The light is transported by fiber bundle 77 to a position close to the objective lens 5 and emanates from an exit end 78 of the fiber bundle 77. A collimating optics 79 is provided for shaping the emanating light to form an illuminating light beam 81 directed to object 9. The embodiment is not limited to using a halogen lamp as a light source. Also other light sources, such as a xenon lamp, may be used.

In the presentation of FIG. 1 the collimating optics 79 is positioned comparatively close to the objective lens 5. Nonetheless, the illuminating light beam 81 is oriented with a relatively high angle with respect to optical axis 7 of objective lens 5. Such high angle between the directions of the illuminating light beam 81 and the main axis 7 of the objective lens may result in an insufficient illumination of the object. In particular in a situation where a surgical method is performed in a deep hole provided in the human body, such as in a human brain for treating an aneurysm, it may not be possible to perceive both the visible light image and the fluorescent light image in superposition with each other. For such and other applications it is preferred to use a configuration of the illuminating system in which the illuminating light beam is oriented with a low angle to the optical axis 7. This may be conventionally achieved by including the objective lens in the beam path of the illuminating light beam, i.e., the illuminating light beam passes through the objective lens, or the objective lens is provided with an aperture penetrated by the illuminating light beam.

Figure 2B:
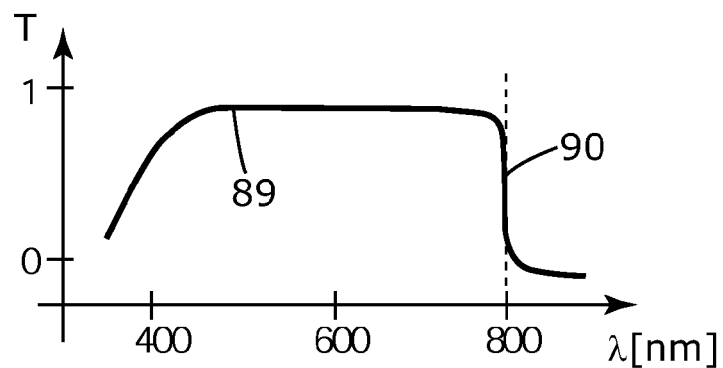

The illuminating system 63 further comprises a filter plate 83 having two filters 84 and 85 disposed adjacent to each other. An actuator 87 controlled by controller 35 is provided for displacing the filter plate 83 in a direction indicated by double arrow 88 in FIG. 1 such that filter 84 is disposed in beam 74 in a first position of plate 83 and that filter 85 is disposed in beam 74 in a second position of plate 83. A transmission characteristics of filter 84 is shown in FIG. 2b as a line 89 and represented in table 1 below:

TABLE 1

| T [%] | λ [nm] |
|---|---|
| <05 | 300-385 |
| =50 | 395-410 |
| >85 | 420-660 |
| >70 | 420-770 |
| =70 | 779 |
| =0.1 | 801 |
| <0.0 | 810-1200 |

It is evident that filter 84 transmits visible light and light with wavelengths up to a flank 90 of 800 nm substantially completely and that wavelengths above flank 90 are substantially not transmitted. Filter 84 is positioned in beam 74 in applications for observing the fluorescence of the fluorescent substance in the inspected object region 9. Flank 90 at 800 nm is at a wavelength higher than the excitation wavelength 59 of ICG such that light beam 81 both excites the fluorescence detected by camera 55, and illuminates the object region with visible light such that the visible light image of the object may be perceived by looking into the oculars 16, 17 and by observing the images detected by cameras 32, 43.

Figure 2C:
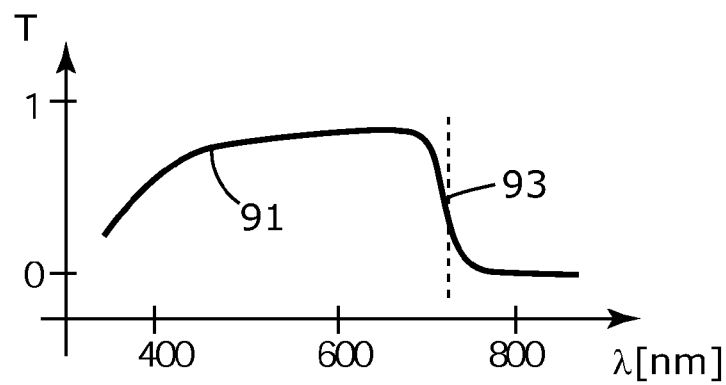

In an application where it is not necessary to observe the fluorescence, the controller 35 drives the actuator 87 to displace filter plate 83 such that filter 84 is disposed in beam 74. A transmission characteristics of filter 85 is schematically illustrated in FIG. 2c as a line 91 and represented in table 2 below:

TABLE 2

| T [%] | λ [nm] |
|---|---|
| <05 | 300-385 |
| =50 | 395-410 |
| >85 | 420-660 |
| >70 | 420-660 |
| =50 | 680-710 |
| <05 | 720-1180 |

It is evident that filter 85 substantially transmits visible light up to a flank 93 of the transmission characteristics 91, and that the filter is substantially non-transmissive for light at wavelengths above flank 93.

Flank 93 is at about 710 nm. The filter 85 is used as a thermal protective filter for eliminating radiation from the illuminating light beam 81 which would otherwise result in an unnecessary heating of the object 9. The flank 93 is well below the maximum excitation wavelength 59 of ICG even though an excitation spectrum of ICG extends to wavelengths below 710 nm. However, a fluorescence of the substance is substantially not excited when filter 85 is disposed in beam 74.

The controller further comprises an image 95 for storing a series of images or image data representing such images detected by camera 55. The 35 is further configured to successively supply the image data stored in memory 95 to display 69 such that display 69 displays the images previously detected by camera 55 as a time series of images. The series of images may be also supplied to the head mounted display 49.

The display of the time series the images may be understood as a film representation of the infrared light images. Such representation will be preferably used in a situation where a process of the fluorescent substance entering a vessel system allows to assess and verify structures or functions of the vessel system. At a time after the fluorescent substance has entered the vessel system the detected image will be substantially stationary in time, and substantially no additional information may be gained from further observation of the infrared light image. Since such process of entering the vessel system is of a relatively short duration of one to five seconds, a surgeon would have to watch the process with highest concentration and memorize the time dependence of the process for each vessel of interest. The possibility of storing the images detected by camera 55 during the process and the possibility to repeatedly display the stored images as a film will help the surgeon in gaining a complete impression of the observed process.

An embodiment of a method of operating the microscopy system 1 will be illustrated below with reference to the flowchart of FIG. 3. At a start of an imaging procedure the thermal protective filter 85 is disposed in the beam path of the illumination system 63, and the controller waits in step S1 for a start button of a switch 97 or some other input means being operated by the surgeon or his assistant. Preferably, the start button 97 will be operated shortly before or after the injection of the fluorescent substance into the patient. In step S3 the actuator removes the thermal protective filter 85 from the beam path and inserts fluorescent imaging filter 84 in the beam path, and in S5 a counter is reset. Thereafter, an image B(0) detected by camera 55 is stored as image data in memory 95 (step S7). This image is also transferred by controller 35 to display 69. Display 69 displays the image such that the surgeon may perceive the image in superposition with the visible light image of the object 9 when looking into the ocular (S9). Thereafter counter is incremented (S11), a next image B(n) is received from camera 55 and stored in memory 95 (S13), and this image B(n) is visualized by display 69 or 51 in step S15.

Since the vessel system under observation does not contain fluorescent substance at the start of the procedure, the first detected images B(n) show substantially no intensities of infrared light. The fluorescent substance propagates through the body of the patient and finally enters the tissue region 9 in the object field of the microscopy objective 3 such that the images B(n) show successively increasing infrared intensities. The controller 35 analyses the intensities of the images B(n) and compares the intensities in step S17 with a first predetermined threshold. If the intensity of the latest detected image B(n) is less than the first threshold processing is continued with step S11. If the intensity of image B(n) is higher than the first threshold this is indicative of a point in time used as a start of a series of detected images which series will be the repeatedly displayed to the user later. The current value of counter n is assigned to a variable nstart in step S19.

Thereafter the counter is incremented (S20), the next image B(n) is obtained and stored (S21) and displayed (S23). The controller 35 compares in step S25 the intensity of the last detected image B(n) with the intensity of the second last image B(n−1) and continues processing at step S20, if the difference between both intensities is higher than a predetermined second threshold value. The second threshold value is chosen such that the condition of step S25 will not be fulfilled shortly after the start of the substance entering the vessel since the intensities will continuously increase at that time. At some later time the concentration of the fluorescent substance will come close to a saturation, and differences between intensities of subsequent images B(n) and B(n−1) will become smaller than the second threshold value. This is indicative of a point in time at which the series of detected images should be terminated. The current value of the counter n is assigned to a variable nend in step S27, and the fluorescent imaging filter 83 is removed from the beam 74 and the thermal protective filter 85 is inserted in beam 74 in step S29.

Thereafter the processing is continued by repeatedly displaying the detected images with displays 69 or 51. For this purpose the counter n is set to the value nstart corresponding to the start of the series of images (S31), in which B(n) is displayed (S33), and the counter n is incremented (S35). If a present value of counter n is below the value nend thereof at the end of the series of images in step S37, processing is at step S33. Otherwise it is decided in step S39 whether button 97 was again operated for indicating an end of the procedure (S39). If the end of the procedure is not indicated, processing is continued at step S31 for displaying the series of images again.

While the above illustrated embodiment uses one single light source for generating the light beam illuminating the object with visible light and for exciting the fluorescence, a further embodiment may use different light sources for generating the visible light and the excitation light, respectively. The light source generating the excitation light may then be switched on and off according to the application.

A further embodiment may include two or plural light beams generated by one single light source or separate light sources wherein each beam includes the visible light and the excitation light.

In the embodiment illustrated above with reference to FIGS. 1 to 3 the microscopy system 1 uses filters 84 and 85 which are transmissive filters. An alternative embodiment may use corresponding reflective filters which may be provided by a suitable coating of reflector 72 of the light source or which may be provided by separate reflectors with desired filter characteristics which separated reflectors may be inserted in the beam path with an actuator under control of controller 35.

In the embodiment illustrated above with reference to FIGS. 1 to 3 the microscopy system 1 with its filters 57, 84 and 85 and filter characteristics shown in FIGS. 2a, 2b, 2c, respectively, is optimized for observing the fluorescence of indocyanine green. In alternative embodiments the above illustrated principles may be applied to an observation of alternative fluorescent substances by adapting edges 90 and 61 of characteristics 89 and 58 to the corresponding excitation wavelengths and fluorescent wavelengths of the alternative fluorescent substance.

Figure 4:
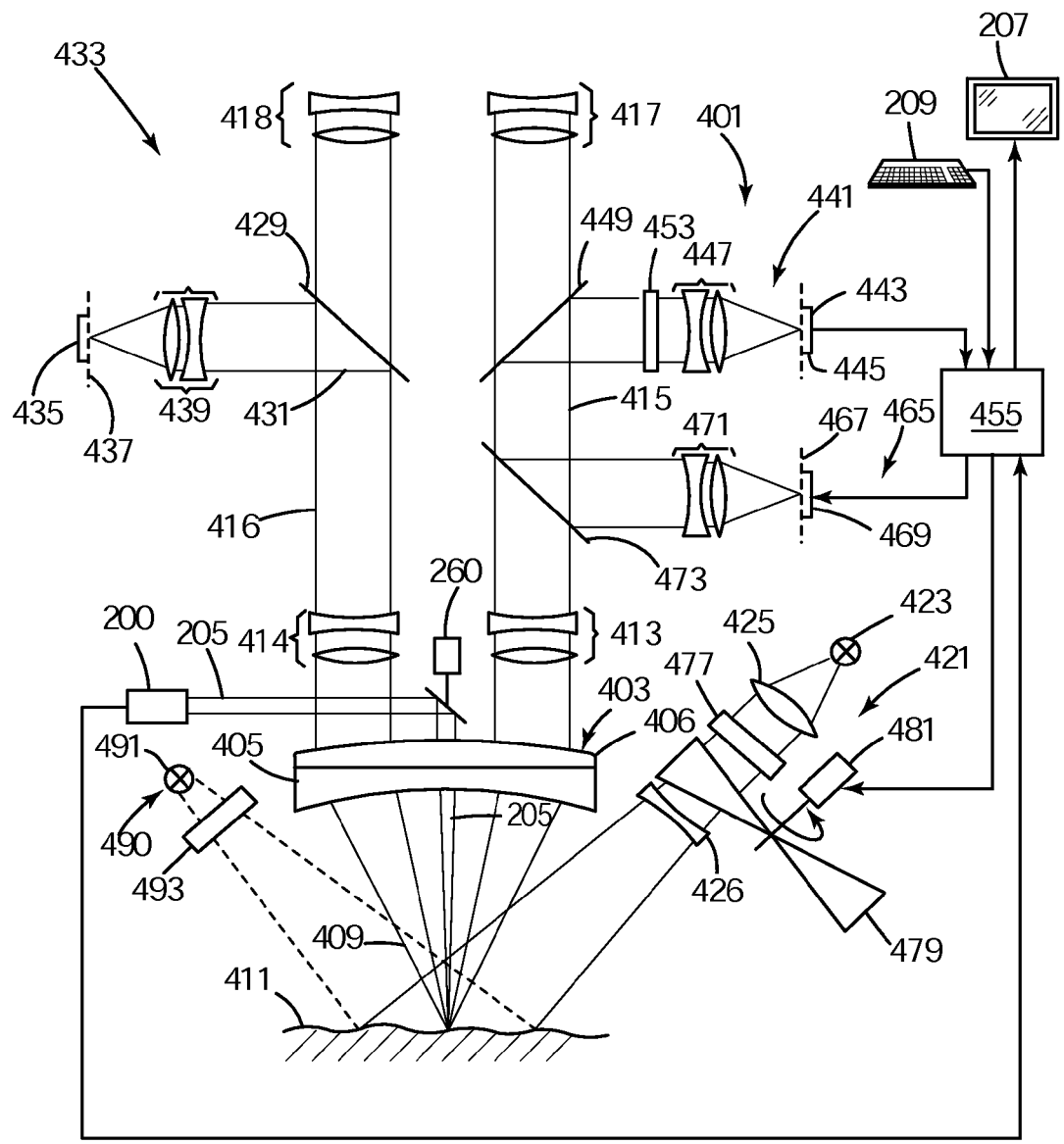
FIG. 4 is a schematic representation of a further embodiment of the microscopy system according to the invention.

FIG. 4 schematically illustrates a beam path of a further embodiment of a microscopy system 401. The microscopy system comprises an objective lens 403 having plural lenses 405 and 406. Lenses 405 and 406 are covered with antireflective coatings such that reflections of visible light at the surfaces of the lenses are reduced. The antireflective coating may be designed such that also reflections of infrared light and near infrared light at the lens surfaces are reduced.

Objective lens 403 receives a divergent beam 409 emanating from an object plane 411 of the objective lens 403. The diverging beam 409 is transformed by the objective lens to provide a substantially parallel beam downstream of the objective lens. Downstream of the objective lens 403 and above the objective lens in the representation of FIG. 4 there are provided two zoom systems 413 and 414 which are schematically indicated in FIG. 4. Each zoom system 413, 414 uses a partial beam 415, 416 respectively and supplies the same to oculars 417, 418 respectively of the microscopy system. A user may perceive a magnified sharp image of object plane 411 by looking into the oculars 417 and 418 with his right and left eyes, respectively. Visible light is used for generating these images of the object plane 411. For this purpose, the object plane 411 is illuminated with visible light supplied by an illumination system 421 comprising a xenon lamp 423 and beam shaping lenses 425 and 426.

The microscopy system 401 further comprises a camera 433 for detecting a substantially sharp image of the object plane with visible light. The camera 433 comprises a CCD camera chip 435 having a light sensitive substrate positioned in an image plane 437. A beam splitter 429 is provided in the partial beam 416 for branching off a beam 431 therefrom and for supplying beam 431 to a camera adapter optics 439 supplying the beam 431 to the camera such that the substantially sharp image of the object plane 411 is generated at the image plane 437. The images detected by camera 433 may be used for documentation or they may be displayed by a display apparatus for displaying the image of the object plane 411 for users who may not directly use the oculars 417, 418. The images of camera 433 may be in particular supplied to a head mounted display of a user.

The microscopy system 1 comprises a camera 441 for detecting images of the object plane with infrared light. Camera 441 comprises a CCD camera chip 443 having a light sensitive substrate positioned in an image plane 445. A camera adapter optics 447 is provided for supplying a beam 451 branched off from the partial beam 451 by a beam splitter 449 to the CCD camera chip 43. The camera adapter optics 447 is configured such that a substantially sharp image of the object plane 411 is generated in image plane 445 with infrared light.

Thus, the cameras 433 and 441 differ from each other in that camera 433 generates a substantially sharp image of the object plane 411 with visible light, and camera 441 generates a substantially sharp image of the object plane with infrared light. According to one conventional definition the infrared light may comprise wavelengths in a range of 820 nm to 870 nm.

A filter 453 is in beam 451 in front of camera 441. Filter 453 is adapted to the fluorescent substance which is used in the application. In the present example the filter 453 is adapted to the fluorescence of the indocyanine green such that it transmits substantially only light of a wavelength range between 820 nm and 870 nm. The fluorescent wavelengths of indocyanine green are within this wavelength range.

According to an alternative embodiment the beam splitter 449 may be covered with a suitable coating such that the beam splitter 449 deflects only infrared light.

Images detected by camera 441 are supplied to a controller or computer 455.

In an application according to one embodiment a tissue to be inspected, such as a human liver is positioned in the object plane 411. Blood vessels extending through the tissue are substantially not visible if the tissue is observed by just using the visible light images provided by oculars 17 and 18. It is not easy to discriminate between blood vessel and surrounding lever tissue from such images. After an intravenous injection of ICG the fluorescent substance will accumulate in the vessels at a higher concentration than in surrounding tissue. An image of the tissue using light in the wavelength range of 820 nm to 870 nm will show higher intensities at locations corresponding to fluorescent vessels as compared to surrounding tissue.

Figure 5A:
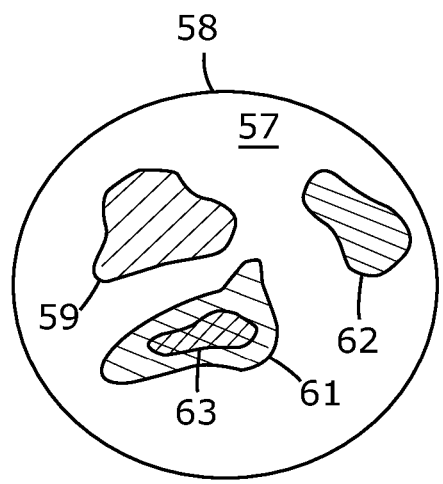
FIG. 5 is a schematic representation of images generated with the microscopy system of FIG. 4.

An example of an image detected by camera 441 and supplied to controller 455 is schematically illustrated in FIG. 5a. A major portion 57 of an imaging field 58 shows a very low intensity. A portion 59 shows a slightly higher intensity, and two portions 61, 62 show even higher intensities. Within portion 61 there is located a portion 63 showing an even higher intensity of infrared radiation. It is assumed that the 62 and 63 are associated with blood vessels, whereas the portion 57 is associated with surrounding tissue. It is further assumed that the portion 59 is associated with surrounding tissue in which some low concentration of fluorescent substance has accumulated.

The microscopy system 1 further comprises a display system 465 comprising an LCD chip 469 positioned in a plane 467. An image displayed with LCD chip 469 is superimposed partial beam 415 by a projection optics 471 and a beam splitter 473. When looking into the ocular 417 the user may perceive a superposition of the visible light image of the object plane and an image representation generated by display 469. The controller 455 may supply an image to display 469 as it is schematically illustrated in FIG. 5a. The image is displayed and perceived by the user with visible light of e.g. blue color. Thus, the user is provided with a visible representation of the infrared image in a superposition with the visible light image. The user may then recognize blood vessels positioned within the object field of the microscopy system 1.

However, the superposition of the visible light image with the image according to FIG. 5a would result in a reduction of the information which may be gained from the visible light image within portions 61 and 62 since these portions are indicated in blue color. To improve this situation the controller 455 performs an analysis of the images received from camera 441. The controller determines those coherent portions of the image showing intensities above a predetermined threshold. Using a suitable predetermined threshold a discrimination may be made between blood vessels and surrounding tissue. In the example shown in FIG. 5a the threshold will be adjusted such that the intensity in the portion 59 is below the threshold, and such that the intensities within portions 62 and 63 are above the threshold.

Figure 5B:
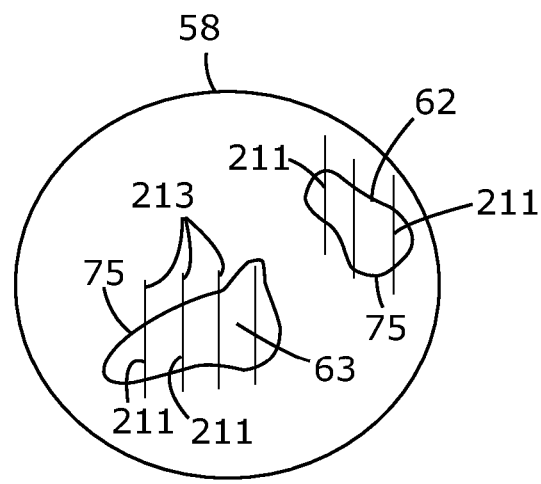

After identifying the coherent portions exceeding the threshold the controller 455 will determine peripheral lines surrounding the coherent regions. Such peripheral lines are associated with a boundary between the coherent portions and the surrounding portions of the image. The controller 455 supplies data representing the peripheral lines to the display 465. The display generates an image of the peripheral lines, and such image is superimposed with the light image as schematically illustrated in FIG. 5b. In the image, only the peripheral lines 75 of portions 61 and 62 are shown in blue color, Thus, the user is provided with the information relating to the blood vessels which are located in an interior of the peripheral lines 75, and the user may still perceive the visible light image of the blood vessels as usual, and he may perform a surgical treatment of these blood vessels while observing the visible light image thereof.

A filter 477 is disposed in a beam path of illumination system 421. Filter 477 is substantially not transmissive for wavelengths of the fluorescent emission of the fluorescent substance. The object will not be illuminated with fluorescent light such that the fluorescence of the substance is visible in the images detected by camera 441 with a high contrast and low background.

Additionally, a filter chopper 479 is disposed in the beam path of the illumination system 421. The filter chopper 479 is rotatably driven by a motor 481 which is controlled by controller 455. The filter chopper comprises plural sectors which are subsequently transmissive and non-transmissive for light at wavelengths in a range between 750 nm and 820 nm. All sectors of the filter chopper 479 are substantially transmissive for visible light. The excitation of the fluorescent substrate is modulated by rotating the filter chopper 479. The intensities of the fluorescent images detected by camera 441 are modulated in time, accordingly, and the controller 455 may analyze the time dependency of the fluorescent image by a method such as a lock-in method for further reducing noise and background in the fluorescent image.

An alternative embodiment of the illumination system illustrated above is indicated by dashed lines in FIG. 4. The alternative illumination system 490 comprises a light source 491 separate from light source 423. Light source 491 is provided for illuminating the object with visible light, whereas light source 423 is only provided for generating the excitation light of the fluorescent substance. Thus, the illumination with visible light is independent from the illumination with excitation light, and a rotation of the chopper wheel 479 may not modulate the illumination with visible light which modulation might disturb the user in observing the visible light image of the object. According to a further embodiment the light source 423 is a laser light source which is rapidly switched on and off by the controller 455 for modulating the excitation light. The light modulating chopper may be omitted in such embodiment.

The microscopy system further comprises an optical coherence tomography (OCT) apparatus 200 emitting an analyzing light beam 205 and directing the analyzing light beam 205 onto a beam scanner 260. Beam scanner 260 comprises a mirror for directing the analyzing light beam onto the object plane 411 and to focus the analyzing light beam 205 onto the object plane. The beam scanner 260 is controlled by controller 455 for selecting the locations at which the analyzing light beam 205 is directed onto the object plane and to change those locations. The OCT apparatus 200 detects depth profile data of the object at the selected location and transmits the depth profile data to controller 455. OCT apparatuses are well known from the art. Examples are given in U.S. Pat. Nos. 5,493,109 and 5,795,295, the full disclosure of which is incorporated herein by reference.

Figure 6:
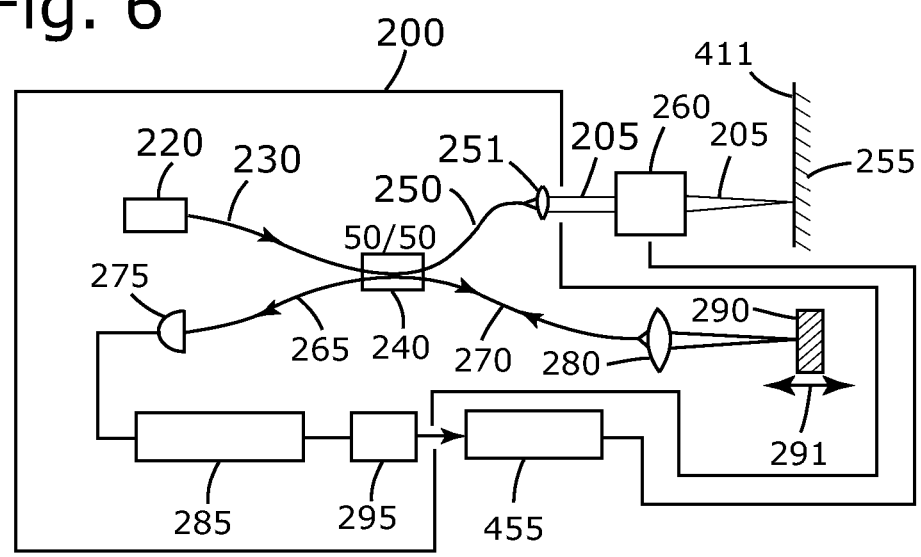
FIG. 6 is a detailed partial illustration of an interferometer apparatus provided in the microscopy system according to FIG. 4.

A function of the OCT apparatus 200 is shortly illustrated with reference to FIG. 6 below. The apparatus 200 comprises white light source 220 emitting radiation coupled into an optical fiber 230. A beam coupler 240 is provided for coupling the radiation into two optical fibers 250 and 270. One partial beam of fiber 270 is directed onto a reference mirror 290 through a lens 280. The partial beam of fiber 250 is collimated through a lens 251 as the analyzing light beam 205 and directed to the beam scanner 260. The beam scanner 260 directs the analyzing light beam 205 onto the object 255 to be inspected. Radiation of the analyzing light beam 205 received from the object is supplied by beam scanner 260 in a reverse direction back to the OCT apparatus 250 and coupled into fiber 250. The radiation reflected back from mirror 290 is again coupled into fiber 270. The beam coupler 240 superimposes the radiation received from the object through fiber 250 and the radiation reflected back from mirror 290 through fiber 270 and couples the superimposed radiations into fiber 265. Fiber 265 supplies the superimposed radiation to a photodetector 275. An output of the photodetector is demodulated by a demodulator 285 and transformed to computer readable data by an analog-digital-converter 295 and supplied to the controller 455.

The detector 275 receiving the radiation from the object 255 and the mirror 290 detects a signal which is increased by interference if optical wavelengths of the two partial beams between the beam splitter 240 and their superposition at the beam splitter 240 are equal within a coherence length of the light source. For achieving such equal optical beam paths, the reference mirror 290 is displaceable in a direction indicated with arrow 291 in FIG. 6. By displacing the mirror 290 and recording the corresponding intensities detected by detector 275 it is possible to detect a depth profile of the object 255 at that location at which the analyzing light beam 205 is directed onto the object 255. Obtaining such depth profile is time consuming since the mirror 290 has to be mechanically displaced.

The controller 455 controls the beam scanner 260 to direct the analyzing light beam 205 to those locations on the object at which depths profiles should be recorded. The controller 455 limits the recording of depths profiles to only those portions or analyzing regions which have been previously determined by controller 455 from the fluorescent light image which are indicated by reference numeral 62 and 63 in FIG. 5b.

The controller 455 controls the beam scanner 260 such that depth profiles are recorded at a plurality of locations positioned on straight lines 213 within portions 62, 63, wherein the straight lines 213 are vertically arranged in the visible field 58 and disposed at a predetermined distance from each other. The depth profiles recorded along lines 211 are displayed on a display 207 of the microscopy system 401. A keyboard 209 or other input means, such as a mouse, may be used for selecting the configuration of the straight lines 213 within the visible field 58, such as an orientation thereof and distance from each other. Further, one of portions 62, 63 may be selected such that depths profiles for the selected portion are not shown on display 207.

It is also possible to display some selected of the depths profiles by imaging system 65 and to superimpose such representations with the visible light image perceived through the ocular such that the user may analyze the depth profile while observing the image of the object through the ocular.

In the above illustrated embodiments indocyanine green is used as the fluorescent substance. However, other fluorescent substances may be also used. In particular, an auto-fluorescence of substances of the human body may be observed. As an alternative or in addition to the analysis of intensities of fluorescent images, also fluorescent half times may be analyzed for discriminating fluorescent regions from each other within the object field.

According to further embodiments the image generated by display apparatus 65 is coupled into partial beam 416 rather than partial beam 415. Alternatively corresponding representations may be coupled into both partial beams.

In the preceding embodiments the peripheral lines 75 are represented as full lines. According to further embodiments, the peripheral lines may be represented as broken lines, dotted lines, dot-dashed lines or other types of lines, or the interior of the coherent portions may be represented as a shaded or hatched region of the image.

Therefore, while the present invention has been shown and described herein in what is believed to be the most practical and preferred embodiments, it is recognized that departures can be made therefrom within the scope of the invention, which is therefore not be limited to the details disclosed herein but is to be accorded the full scope of the claims so as to embrace any and all equivalent methods and apparatus.

The invention claimed is:

1. A method of operating a surgical microscope, wherein the surgical microscope comprises:

a camera having a light detecting component;

microscopy optics having a first beam path for optically imaging an object region onto the light detecting component of the camera for generating image data representing intensities of images of the object region; and an illumination system configured to direct at least one illuminating light beam onto the object region;

wherein the illumination light beam includes visible light from a broad wavelength range and excitation light of a fluorescence of indocyanine green of about 800 nm;

wherein the illumination system comprises a first filter which is positionable at the first filter's first position in which the first filter is disposed in the illumination light beam and the first filter's second position in which the first filter is not disposed in the illumination light beam;

wherein the first filter is configured to eliminate light with wavelengths greater than a predetermined wavelength from the illuminating light beam and to allow the visible light of wavelengths up to the predetermined wavelength to traverse the first filter, wherein the predetermined wavelength is in a range of one of 690 nm to 780 nm;

wherein the illumination system comprises a second filter which is positionable at the second filter's fall first position in which the first filter is disposed in the illumination light beam;

wherein the second filter is configured to eliminate light with wavelengths greater than 800 nm from the illuminating light beam and to allow light of wavelengths up to 800 nm to traverse the second filter; and wherein the method comprises:

providing a combined fluorescence and visible light observation mode of the surgical microscope by positioning the first filter in its second position and the second filter in its first position; then recording at least one fluorescence image of the object region using the camera; and then terminating the combined fluorescence and visible light observation mode and providing a pure visible light observation mode by moving the first filter from its second position to its first position.

2. The method according to claim 1, wherein the terminating of the combined fluorescence and visible light observation mode and providing the pure visible light observation mode comprises moving the second filter from its first position to the second filter's second position.

3. The method according to claim 2, wherein the terminating of the combined fluorescence and visible light observation mode and providing the pure visible light observation mode comprises moving the first and second filters between first and second configurations, wherein the first filter is in its first position and the second filter is in its second position in the first configuration and wherein the first filter in its second position and the second filter is in its first position in the second configuration.

4. The method according to claim 1, further comprising a control device configured to analyze the image data and to control the movement of the first filter from its second position to its first position based on an analysis of the image data.

5. The method according to claim 4, wherein the control device is configured to analyze the intensities of the images represented by the image data and to control the movement of the first filter from its second position to its first position based on an analysis of the intensities of the images.

6. The method according to claim 4, wherein the control device is configured to analyze changes of the intensities of the images represented by the image data and to control the movement of the first filter from its second position to its first position based on an analysis of the changes of the intensities of the images.

7. The method according to claim 1, wherein the image data represent images of the object region with light including wavelengths of a wavelength range comprising a fluorescent emission wavelength of the indocyanine green accumulated in the object region.

8. The method according to claim 7, wherein the fluorescent emission wavelength of the indocyanine green is greater than the predetermined wavelength.

9. The method according to claim 1, wherein the illumination system includes a light source emitting the visible light, the excitation light and thermal radiation.

10. The method according to claim 9, wherein the light source is one of a xenon lamp and a halogen lamp.

11. The method according to claim 1, wherein the microscopy optics has at least one second beam path including an ocular for optically imaging object region to a user's via the ocular.

12. A surgical microscope comprising:

a camera having a light detecting component;

microscopy optics having a first beam path for optically imaging an object region onto the light detecting component of the camera for generating image data representing intensities of images of the object region; and an illumination system configured to direct at least one illuminating light beam onto the object region;

wherein the illumination light beam includes visible light from a broad wavelength range and excitation light of a fluorescence of indocyanine green of about 800 nm;

wherein the illumination system comprises a first filter which is positionable at the first filter's first position in which the first filter is disposed in the illumination light beam and the first filter's second position in which the first filter is not disposed in the illumination light beam;

wherein the first filter is configured to eliminate light with wavelengths greater than a predetermined wavelength from the illuminating light beam and to allow the visible light of wavelengths up to the predetermined wavelength to traverse the first filter, wherein the predetermined wavelength is in a range from 690 nm to 780 nm;

wherein the illumination system comprises a second filter which is positionable at the second filter's first position in which the first filter is disposed in the illumination light beam;

wherein the second filter is configured to eliminate light with wavelengths greater than 800 nm from the illuminating light beam and to allow light of wavelengths up to 800 nm to traverse the second filter; and further comprising a combined fluorescence and visible light observation mode of the surgical microscope by positioning the first filter in its second position and the second filter in its first position;

wherein at least one fluorescence image of the object region using the camera is recorded; and wherein the combined fluorescence and visible light observation mode is terminated and a pure visible light observation mode is provided by moving the first filter from its second position to its first position.

13. The surgical microscope according to claim 12, wherein the combined fluorescence and visible light observation mode is terminated and the pure visible light observation mode is provided by moving the second filter from its first position to the second filter's second position.

14. The surgical microscope according to claim 13, wherein the combined fluorescence and visible light observation mode is terminated and the pure visible light observation mode is provided by moving the first and second filters between first and second configurations, wherein the first filter is in its first position and the second filter is in its second position in the first configuration and wherein the first filter in its second position and the second filter is in its first position in the second configuration.

15. The surgical microscope according to claim 12, further comprising a control device configured to analyze the image data and to control the movement of the first filter from its second position to its first position based on an analysis of the image data.

16. The surgical microscope according to claim 15, wherein the control device is configured to analyze the intensities of the images represented by the image data and to control the movement of the first filter from its second position to its first position based on an analysis of the intensities of the images.

17. The surgical microscope according to claim 15, wherein the control device is configured to analyze changes of the intensities of the images represented by the image data and to control the movement of the first filter from its second position to its first position based on an analysis of the changes of the intensities of the images.

18. The surgical microscope according to claim 12, wherein the image data represent images of the object region with light including wavelengths of a wavelength range comprising a fluorescent emission wavelength of the indocyanine green accumulated in the object region.

19. The surgical microscope according to claim 18, wherein the fluorescent emission wavelength of the indocyanine green is greater than the predetermined wavelength.

20. The surgical microscope according to claim 12, wherein the illumination system includes a light source emitting the visible light, the excitation light and thermal radiation.

21. The surgical microscope according to claim 20, wherein the light source is one of a xenon lamp and a halogen lamp.

22. The surgical microscope according to claim 12, wherein the microscopy optics has at least one second beam path including an ocular for optically imaging object region to a user's via the ocular.

* * * * *

UNITED STATES PATENT AND TRADEMARK OFFICE
CERTIFICATE OF CORRECTION

| | | |
|---|---|---|
| PATENT NO. | : 8,810,907 B2 | Page 1 of 1 |
| APPLICATION NO. | : 13/193759 | |
| DATED | : August 19, 2014 | |
| INVENTOR(S) | : Michael Haisch et al. | |

It is certified that error appears in the above-identified patent and that said Letters Patent is hereby corrected as shown below:

IN THE CLAIMS

Column 16, Claim 1, Line 60, delete "mined wavelength is in a range one of 690 nm to 780 nm" and insert -- mined wavelength is in a range from 690 to 780 nm -- therefor.

Column 16, Claim 1, Line 63, delete "which is positionable at the second filter's fall first position" and insert -- which is positionable at the second filter's first position -- therefor.

Signed and Sealed this
Seventeenth Day of March, 2015

Michelle K. Lee
*Director of the United States Patent and Trademark Office*